United States Patent
Heid

(10) Patent No.: US 11,986,354 B2
(45) Date of Patent: May 21, 2024

(54) ULTRASONIC APPARATUS FOR MEDICAL EXAMINATION USING ULTRASONIC WAVES

(71) Applicant: H-Next GmbH, Erlangen (DE)

(72) Inventor: Oliver Heid, Erlangen (DE)

(73) Assignee: H-NEXT GMBH, Erlangen (DE)

( * ) Notice: Subject to any disclaimer, the term of this patent is extended or adjusted under 35 U.S.C. 154(b) by 15 days.

(21) Appl. No.: 16/970,751

(22) PCT Filed: Jan. 25, 2019

(86) PCT No.: PCT/EP2019/051848
§ 371 (c)(1),
(2) Date: Aug. 18, 2020

(87) PCT Pub. No.: WO2019/179675
PCT Pub. Date: Sep. 26, 2019

(65) Prior Publication Data
US 2021/0093299 A1   Apr. 1, 2021

(30) Foreign Application Priority Data
Mar. 21, 2018   (DE) ............ 10 2018 204 357.4

(51) Int. Cl.
  A61B 8/08   (2006.01)
  A61B 8/00   (2006.01)
  G01S 15/89  (2006.01)

(52) U.S. Cl.
  CPC .......... *A61B 8/5207* (2013.01); *A61B 8/4472* (2013.01); *A61B 8/4494* (2013.01); *A61B 8/56* (2013.01); *G01S 15/8915* (2013.01)

(58) Field of Classification Search
  CPC ... A61B 8/5207; A61B 8/4472; A61B 8/4494; A61B 8/56; A61B 8/4488; G01S 15/8915; G01S 7/5208; G10K 11/34
  (Continued)

(56) References Cited

U.S. PATENT DOCUMENTS 6,290,648 B1 *  9/2001  Kamiyama .......... A61B 8/4245
                                              128/916
2008/0110266 A1  5/2008  Randall et al.
(Continued)

FOREIGN PATENT DOCUMENTS

EP   2614775 A1   7/2013

OTHER PUBLICATIONS

International Search Report issued in corresponding PCT Application No. PCT/EP2019/051848 on May 8, 2019.

*Primary Examiner* — Jason M Ip
*Assistant Examiner* — Renee C Langhals
(74) *Attorney, Agent, or Firm* — CARTER, DELUCA & FARRELL LLP

(57) ABSTRACT

An ultrasonic apparatus for medical examination using ultrasonic waves, comprising a movable transducer probe which includes a transducer array of electroacoustic transducers for transmitting ultrasonic signals into a patient body and receiving as analog raw data ultrasonic echoes; the transducer probe configured to generate digital raw data based on the received analog raw data which comprises measurement data sets for temporally consecutive measurement time intervals, and is configured to transmit the digital raw data via a digital data interface; a computer device configured to buffer the respective measurement data sets of the digital raw data and is configured to carry out a digital beamforming for each of the buffered measurement data sets, to obtain a reconstructed image of the tissue sector, and generate, based on the reconstructed images, an image stream with a predetermined image refresh rate and supply it to a display means which reproduces the image stream.

10 Claims, 2 Drawing Sheets

(58) Field of Classification Search
USPC .......................................................... 600/443
See application file for complete search history.

(56) References Cited

U.S. PATENT DOCUMENTS

| | | |
|---|---|---|
| 2008/0294046 A1 | 11/2008 | Chiang et al. |
| 2013/0079639 A1 | 3/2013 | Hoctor et al. |
| 2014/0058266 A1* | 2/2014 | Call .................. A61B 8/14 600/443 |
| 2016/0270763 A1* | 9/2016 | Hayes ............... A61B 8/5207 |
| 2017/0128040 A1* | 5/2017 | Kim .................. A61B 8/469 |
| 2017/0219704 A1* | 8/2017 | Call .................. A61B 8/565 |
| 2018/0064423 A1* | 3/2018 | Kawashima ......... A61B 8/5292 |

* cited by examiner

ULTRASONIC APPARATUS FOR MEDICAL EXAMINATION USING ULTRASONIC WAVES

CROSS REFERENCE TO RELATED APPLICATIONS

This application is a national phase of PCT Application No. PCT/EP2019/051848 filed on Jan. 25, 2019, which claims the benefit of and priority to German Patent Application No. 10 2018 204 357.4, filed on Mar. 21, 2018, each of which are hereby incorporated by reference herein in their entirety.

TECHNICAL FIELD

The invention relates to an ultrasonic apparatus for medical examination using ultrasonic waves.

BACKGROUND

In medical diagnostics, ultrasonic apparatuses are often used to examine human or animal tissue by detecting ultrasonic echoes. To do this, a transducer probe is pressed on above the tissue sector to be examined and ultrasonic waves are sent into the tissue sector by means of an array of electroacoustic transducers. The resulting ultrasonic echoes are detected by means of the transducers, wherein from these ultrasonic echoes an image of the tissue sector is reconstructed, which can be two-dimensional or three-dimensional, depending on the number and arrangement of the electroacoustic transducers.

During the processing of the detected ultrasonic echoes, the obtained analog samples are digitized and subjected to a so-called beamforming, in which the samples of the various electroacoustic transducers are suitably time-shifted and added together in order to reconstruct the location of reflectors in the direction of tissue depth as well as in the angular direction relative to the array of electroacoustic transducers. Usually, the signal processing of the ultrasonic echoes detected by the transducer probe is performed in a bulky e box where the analog electrical reception signals of the transducers are transmitted via a coaxial cable bundle. The device box can, for example, be installed in a trolley in combination with a keyboard and a display unit.

The beamforming described above is currently carried out synchronously with the clocking of the analog-to-digital converter which is used to digitize the analog samples. The problem here is that in a measurement operation involving the transmission of at least one ultrasonic pulse and the reception of its echoes over a predetermined period of time, only tissue positions along a beam in one angular direction can be reconstructed by means of the beamforming. Thus, in order to obtain an image of the entire tissue sector, the same measuring operations must be repeated several times, wherein for each measuring operation the beamforming is adapted accordingly in order to reconstruct the tissue locations in a different angular direction. In this manner, a fan of different angular directions is obtained which adds up to the image. Indeed there are also ultrasonic apparatuses that use several beamforming calculation units in parallel for different angular directions. However, this increases the complexity of the ultrasonic apparatus.

To reduce the size of ultrasonic apparatuses, it is known from the state of the art to integrate in the transducer probe also a part of the signal processing which is usually carried out in a device box. In particular, it is known to install an analog-to-digital converter in combination with a beamforming computer unit in the transducer probe and then to transfer the image data obtained from the beamforming to an image forming and display unit via a data interface. However, there is the problem that the beamforming computer unit requires a high computing power and thus leads to a strong heating which is not desired in the transducer probes which are usually guided manually by a user. As a consequence, only a small number of electroacoustic transducers are installed in the transducer probe to limit the computing power required for the beamforming. However, this leads to a low image resolution and low image refresh rates. In addition, the problem remains that a beamforming operation always can only be performed for one angular direction of the corresponding tissue sector.

SUMMARY

It is the object of the invention to create an ultrasonic apparatus for medical examination using ultrasonic waves, which is simple in structure and inexpensive to manufacture, while providing ultrasonic images having a high quality.

This object is achieved by the ultrasonic apparatus according to claim 1. Further developments of the invention are defined in the dependent claims.

The ultrasonic apparatus according to the invention is used for medical examination of the human or animal body. For this purpose, the ultrasonic apparatus comprises a movable transducer probe which can be positioned on a patient's body. The patient can be a human or an animal. Preferably, the movable transducer probe is configured such that it can be held and guided by the hand of a user (in particular a physician). This allows the user to place the transducer probe at any position on the patient's body in order to examine the underlying tissue by means of ultrasonic waves.

The movable transducer probe comprises a transducer array of electroacoustic transducers to transmit ultrasonic signals into the body and to receive ultrasonic echoes of the transmitted ultrasonic signals as analog raw data. Preferably, the electroacoustic transducers are piezoelectric elements. Depending on the configuration of the ultrasonic apparatus, the number of electroacoustic transducers can vary. Often transducer arrays of 128 electroacoustic transducers are used. A respective transducer can generate ultrasonic waves in a transmitting mode by applying an electric voltage. In addition, each transducer can also detect ultrasonic waves in a receiving mode in which no electrical voltage is applied to the respective transducer.

The movable transducer probe of the ultrasonic apparatus according to the invention comprises an analog-to-digital converter configured to generate digital raw data in dependence on the received analog raw data, wherein the digital raw data comprise measurement data sets for temporally consecutive measurement time intervals. A respective measurement data set comprises ultrasonic echoes from a (two-dimensional and optionally also three-dimensional) tissue sector of the body, wherein the ultrasonic echoes result from a transmitting operation of one or more ultrasonic signals by at least one transducer in transmitting mode. The ultrasonic echoes are represented by samples for sample instants of the respective measurement time interval for a plurality of receiving channels from, respectively, at least one transducer in receiving mode. In a preferred variant of the invention, the number of receiving channels corresponds to the number of transducers, i.e. each transducer represents a receiving channel via which a corresponding sample is detected in the receiving mode on the basis of reflected ultrasonic echoes.

In a variant of the invention, only a single transducer is used for transmitting ultrasonic echoes during the transmitting operation. Normally, different transducers are used for transmission over consecutive measurement time intervals. Usually, after the transmitting operation, all transducers of the array are switched to receiving mode.

The ultrasonic apparatus according to the invention further comprises a digital data interface via which the transducer probe is coupled to a separate computer device not belonging to the transducer probe. In other words, the computer device is a component separate from the movable transducer probe. The transducer probe is further configured to transmit the digital raw data, preferably directly without buffering, via the digital data interface. In other words, the digital raw data are streamed by the transducer over the digital data interface. Preferably, the data rate for transmitting the raw data via this data interface is at least 1 GB/s.

The separate computer device, which is part of the ultrasonic apparatus according to the invention, comprises a raw data buffer memory in which the respective measurement data sets of the digital raw data are buffered. In other words, each measurement data set transmitted via the digital data interface is temporarily stored in the raw data buffer memory for a certain period of time, wherein the period of time depends on the size of the buffer memory. In a preferred variant, a so-called circular buffer is used as the buffer memory.

The separate computer device is further configured to carry out a respective digital beamforming for each of the buffered measurement data sets by a time-delayed addition of samples, in order to determine image values from a plurality of tissue locations at different tissue depths and with several tissue locations for each tissue depth, i.e. for different angular directions and different tissue depths. The tissue locations preferably cover the entire tissue sector. In this way, a reconstructed image of the tissue sector is obtained. Depending on the configuration of the transducer probe, a two-dimensional or three-dimensional image can thus be reconstructed.

In other words, due to the use of the raw data buffer memory, the digital beamforming runs decoupled from the clocking of the analog-to-digital converter and thus asynchronous to this clocking. Due to the buffering of the respective measurement data sets, the digital beamforming can be carried out several times for the corresponding measurement data set for different angular directions, so that a reconstructed image of the entire tissue sector can be generated with one measurement data set.

The computer device used in the ultrasonic apparatus according to the invention is further configured to generate, based on the reconstructed images, an image stream of temporally consecutive reconstructed images or of images calculated therefrom with a predetermined image refresh rate, and to supply it to a display means (in particular a display) which reproduces the image stream. In other words, the reproduction of the images can be suitably adjusted to the duration of the beamforming so that an image stream with a desired image refresh rate can be generated and displayed. The display means is a component part of the ultrasonic apparatus according to the invention.

The ultrasonic apparatus according to the invention has the advantage that no special real-time demands must be made on the computer device due to the decoupling of the beamforming from the digitization of the raw data. Thus, commercially available PC components can be used for the computer device, wherein the operation of beamforming and the generation of the image stream can be realized by software running on a processor of a commercially available PC motherboard. In addition, the ultrasonic apparatus according to the invention ensures that the beamforming process is not carried out in the transducer probe, which means that requirements for a lowest possible heat development in the transducer probe can be met.

In a preferred variant of the ultrasonic apparatus according to the invention, a synchronizable display is used as a display means, the image refresh rate of which can be varied. In this way, it is possible to compensate for any fluctuations in the image refresh rate of the generated image stream, thereby avoiding image artifacts that can occur with non-synchronizable displays. Examples of synchronizable displays are known as AMD Freesync or Nvidia G-Sync.

In a particularly preferred embodiment of the ultrasonic apparatus according to the invention, the raw data buffer memory is adapted for the simultaneous buffering of a plurality of consecutive measurement data sets, i.e. several measurement data sets are provided simultaneously in the raw data buffer memory. This variant is preferably combined with a computer device which is configured to determine respective reconstructed images for several of the plurality of buffered measurement data sets temporally in parallel. In this way, the determination of the reconstructed images can be accelerated, and thus a higher image refresh rate can be achieved.

In a further preferred variant of the ultrasonic apparatus according to the invention, the computer device is configured such that the images of the image stream are each calculated as an averaging of several temporally consecutive reconstructed images. In this way, the image quality can be improved.

In another preferred variant, the specified image refresh rate of the image stream is 50 Hz or more, e.g. 60 Hz or 75 Hz. With these frequencies it is ensured that the images of the image stream merge into one another for the human eye, so that no flickering or jitter is perceived.

In another preferred variant of the ultrasonic apparatus according to the invention, the computer device is further configured to determine digital control data based on which the operation of the transducers of the transducer array for transmitting ultrasonic signals and for receiving ultrasonic echoes for the consecutive measurement time intervals is determined. The computer device thereby comprises a control data buffer memory (preferably a circular buffer) in which the digital control data are buffered. Furthermore, the transducer probe is configured to read out the digital control data, preferably directly without buffering, via the digital data interface or an additional digital data interface between the transducer probe and the computer device and, based on these read-out control data, to drive the transducers of the transducer array.

The control data are thus determined in advance with the computer device and then used during the driving of the transducers. By using the control data buffer memory, the generation of the control data is decoupled from the use of the same in the transducer probe. In this way it is possible to generate the control data by a computer device without special real-time requirements. In particular, a conventional PC can be used to generate the control data, wherein on its processor runs software that generates the control data. Preferably, the data rate for reading out the control data via the corresponding digital data interface is at least 1 GB/s.

Depending on the configuration, the digital data interface may comprise or represent a wired data interface and/or a wireless data interface. The additional digital data interface mentioned above can be configured in the same way. In a preferred embodiment, the digital data interface and/or the additional digital data interface comprises or is a PCI Express interface known per se. High data rates can be achieved via such an interface. The PCI Express standard is well known from the state of the art and the PCI Express interface is not limited to a specific version of the standard or of the data lines used in it.

In another preferred embodiment, the transducer probe of the ultrasonic apparatus according to the invention comprises a high voltage transmitter for generating high voltage signals which are supplied via a switch array of transmit-receive switches to the transducer array for generating ultrasonic waves by one or more transducers in transmitting mode, wherein the transducers of the transducer array can be switched by the switch array into the transmitting mode or the receiving mode. If the above described buffering of control data is used in this variant, the control data are processed by the high voltage transmitter, which generates corresponding high voltage signals based on this control data. Furthermore, the control data cause the switch array to be switched such that all transducers are decoupled from the high voltage transmitter in the receiving mode.

In a further embodiment of the ultrasonic apparatus according to the invention, the transducer probe comprises a preamplifier which is configured to amplify the analog raw data before supplying them to the analog-to-digital converter. In this case, the analog-to-digital converter digitizes the amplified raw data.

BRIEF DESCRIPTION OF THE DRAWINGS

An embodiment of the invention is described in detail below with respect to the attached figures, in which.

DETAILED DESCRIPTION

Figure 1:
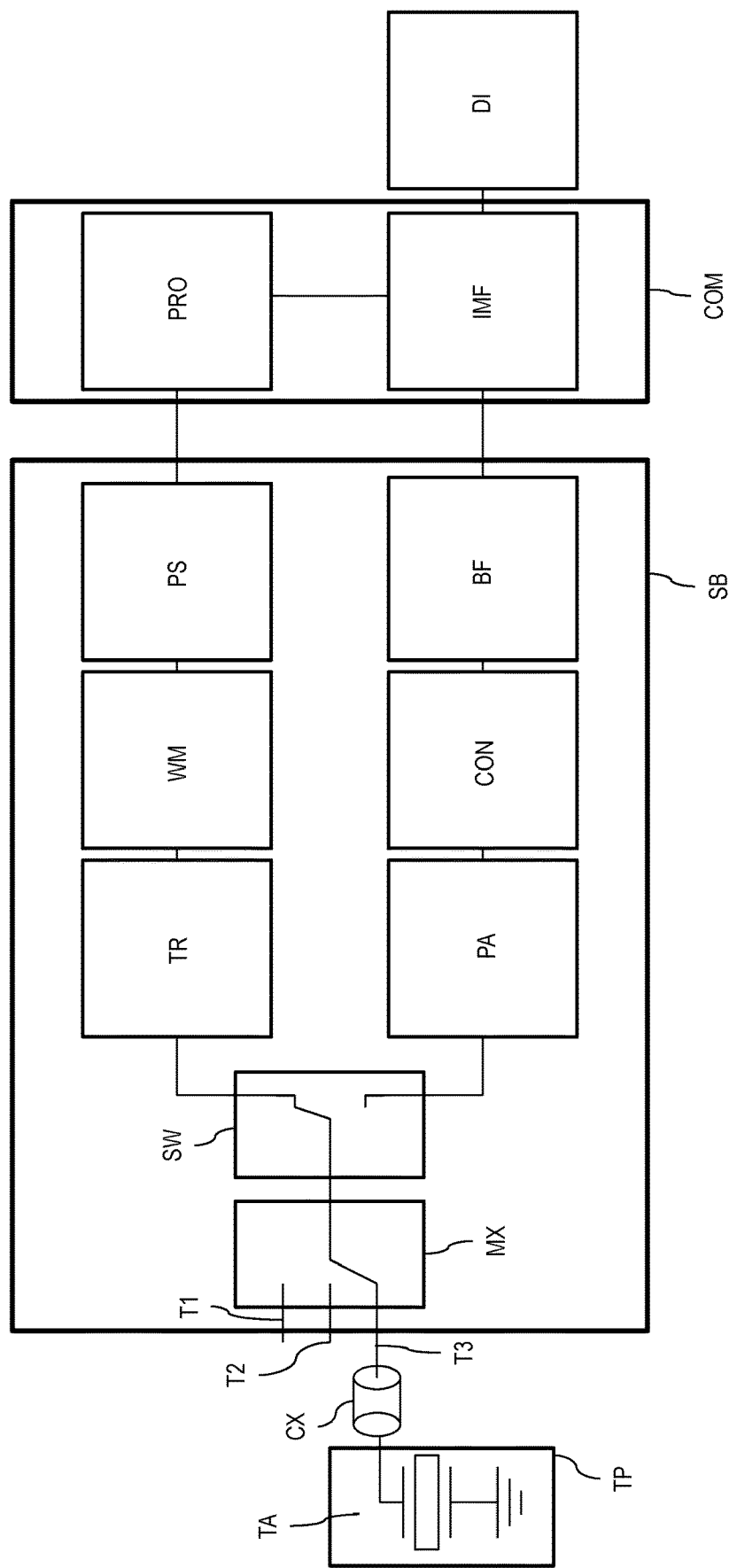
FIG. 1 shows a schematic view of a medical ultrasonic apparatus according to the state of the art.

Before describing an embodiment of an ultrasonic apparatus according to the invention, the structure of an ultrasonic apparatus known per se is first described, which is shown in FIG. 1.

The ultrasonic apparatus according to FIG. 1 comprises a movable transducer probe (TP) which can be guided by the hand of a user and placed on the skin of a patient in order to examine the parts of the body lying under the skin by means of ultrasound. For this purpose, the transducer probe comprises a transducer array TA consisting of a plurality of electroacoustic transducers (e.g. 128 transducers), wherein this array is only schematically indicated by the representation of a single transducer. Usually, the electroacoustic transducers are designed as piezo elements through which ultrasonic signals can be emitted by applying a high voltage. Likewise, corresponding ultrasonic echoes can be received via the piezo elements. The ultrasonic signals are emitted as sound pulses with a repetition rate of several kHz.

Switching between a transmitting mode and a receiving mode of a corresponding piezo element or transducer is enabled by a switch array of transmit/receive switches, which is designated in FIG. 1 with reference sign SW and is explained in more detail below. For the sake of clarity, the switch array is only indicated by one switch.

Movable transducer probe TP is connected via a coaxial cable bundle CX to a device box SB, which is also referred to as scanner box in the following. This device box is a bulky component which contains the essential components for signal processing of the ultrasonic echoes received via transducer probe TP. A data processor or computer COM in the form of a PC is connected to the device box, which PC in turn is connected to a display DI. Usually, the scanner box, the computer and the display form a unit, which is integrated e.g. in a trolley. In addition, the computer can also be part of the device box.

Scanner box SB comprises three ports T1, T2 and T3, which are coupled to a multiplexer MX via which one of these ports can be selected. At each port a separate transducer probe can be connected via a corresponding coaxial cable bundle. Multiplexer MX is used to select the transducer probe that is to be used currently to detect the ultrasonic echoes. FIG. 1 shows merely one single transducer probe TP which is coupled to port T3, where it is connected to the other components of scanner box SB via multiplexer MX.

Multiplexer MX is followed by the above mentioned switch array SW which comprises a plurality of transmit-receive switches, the number of which corresponds to the number of transducers in transducer array TA. In other words, a transmit-receive switch is provided for each transducer. By switching a corresponding transmit-receive switch to the transmitting mode, the associated transducer is connected to a high voltage transmitter TR which generates ultrasonic waves by supplying corresponding high voltage signals to the transducer. If, on the other hand, the corresponding switch is switched to the receiving mode, samples of ultrasonic echoes detected by transducer probe TP are forwarded to a receiving path comprising a preamplifier PR, an analog-to-digital converter CON and a beamformer BF.

Usually, voltages between ±10 V and ±100 V are supplied to the transducers by means of high voltage transmitter TR. The high voltage transmitter is connected to a waveform memory WM and a so-called pulse sequencer PS. The pulse sequencer represents a sequence control system that determines the transmission of ultrasonic pulses and the reception of ultrasonic echoes at corresponding measurement time intervals. For ultrasonic pulses to be transmitted, the pulse sequencer reads the waveform of the corresponding pulse from the waveform memory in the form of a voltage pattern of high voltages. This voltage pattern is supplied to the high voltage transmitter to generate the corresponding high voltages. In addition, the pulse sequencer controls the switches of switch array SW in order to switch the respective switches to the transmitting or receiving state according to the desired measurement sequence. Pulse sequencer PS is realized as an FPGA (FPGA=Field Programmable Gate Array), for example. The pulse sequencer is connected to processor PRO (i.e. the CPU) of computer COM. Instructions for carrying out ultrasonic measurements are sent to the pulse sequencer via the processor.

The ultrasonic echoes received via transducer probe TP are amplified by preamplifier PA (PA=Pre-Amplifier). The amplifier contains a pre-amplifier element for each individual transducer, which amplifies the received signals of the corresponding transducer. The data received in pre-amplifier PA represent analog raw data which contain consecutive measurement data sets. A respective measurement data set refers to a single measurement carried out with transducer probe TP. In such a single measurement, one or more ultrasonic signals are emitted by one or more transducers of transducer array TA according to a predetermined scheme and then, within a predetermined measurement time interval, the ultrasonic echoes caused by reflections in the tissue sector into which the ultrasonic signals were irradiated by transducer probe TP are detected. The length of the measurement time interval can be used to determine the tissue depth up to which ultrasonic echoes are to be received and further processed.

Usually, after the transmission of ultrasonic signals, all transducers are switched to receiving mode by means of switch array SW. Consequently, samples are obtained for each transducer which are obtained for a plurality of sampling instants within the measurement time interval corresponding to a sampling frequency. For a respective measurement time interval, the raw data thus comprise a corresponding measurement data set which comprises, for a plurality of sampling instants, respective samples for all transducers, wherein a respective sample represents the received ultrasonic echo at a sampling instant.

The amplified analog raw data are supplied to an analog-to-digital converter CON, which comprises an A/D converter element for the samples of each electroacoustic transducer. The amplified samples are digitized in the individual A/D converter elements. Analog-to-digital converter CON is clocked at a predetermined frequency and generates a number of digital data streams corresponding to the number of electroacoustic transducers, which represent ultrasonic echoes from increasing tissue depth for respective measurement time intervals. The digital data streams of the analog-to-digital converter are then supplied to a beamforming computer unit BF (BF=beamforming), which is also referred to as a beamformer in the following and is realized as an FPGA, for example. In this beam former, the samples of the different electroacoustic transducers are time-delayed according to a phased array in a manner known per se, so that the time-delayed samples represent the reception of an ultrasonic echo starting from the same reflection point in the tissue. The correspondingly time-delayed samples are added and represent a location in the examined tissue in a predetermined angular direction and at a predetermined tissue depth starting from the transducer array. The corresponding location represents an image point in the ultrasonic image generated later.

As a result of the beamforming carried out in beamformer BF, pixel values (i.e. the sum of correspondingly time-delayed samples) are finally obtained for each measurement time interval, namely for different points in time and thus different tissue depths, but only in a single angular direction. This is due to the fact that the beamforming of beamformer BF is carried out synchronously with the generation of the digital data by analog-to-digital converter CON, so that the beamformer can always set only one time delay for the respective samples and thus can only determine pixel values for one angular direction. Consequently, in order to reconstruct a two-dimensional and possibly also three-dimensional image of the entire tissue sector, it is necessary to carry out the same measurement several times in succession by emitting corresponding ultrasonic signals, wherein for each measurement the beamforming is carried out by adjusting the time delay for a different angular direction. As an option, it is also possible to install several beamformers BF in parallel in device box SB, which, however, causes considerable additional effort and considerable additional costs.

The pixel values obtained by beamformer BF are finally transferred to computer COM, which generates a corresponding image on display DI in a manner known per se using an image former unit IMF (IMF=image former). The function of the image former unit is usually realized by the graphic chip of computer COM, which may also be part of central processor PRO. Usually, images are used for the depiction on display DI which represent an averaging of several consecutive images obtained by the beamforming. The image refresh rate of display DI is fixed, so that the displayed image sequence may suffer from image artifacts such as jitter and tearing (switching between images during image formation).

The sonic speed in biological tissue is about 1450 m/s, so that an ultrasonic echo from e.g. 15 cm depth has a travel time of about 200 μs. Thus, 5000 measurements per second can be carried out for this tissue depth. A data acquisition for a tissue sector with e.g. 125 angular directions thus takes between e.g. 1 ms and more than 100 ms, depending on the set maximum measuring depth, the number of angular directions and the number of images used for averaging.

As can be derived from the above description, the conventional ultrasonic apparatus according to FIG. 1 has the disadvantage that several measurements are required to reconstruct an image of a tissue sector by means of beamforming. This is due to the fact that the beamforming synchronized with the clocking of the analog-to-digital converter can always only calculate pixels from one angular direction per measurement. Although several beamformers can be used to circumvent this problem, this is very effortful and cost-intensive. In addition, image artifacts can occur when displaying the image stream. Furthermore, the dimensions of the ultrasonic apparatus are very large, since a device box in combination with a computer is required for signal processing.

Figure 2:
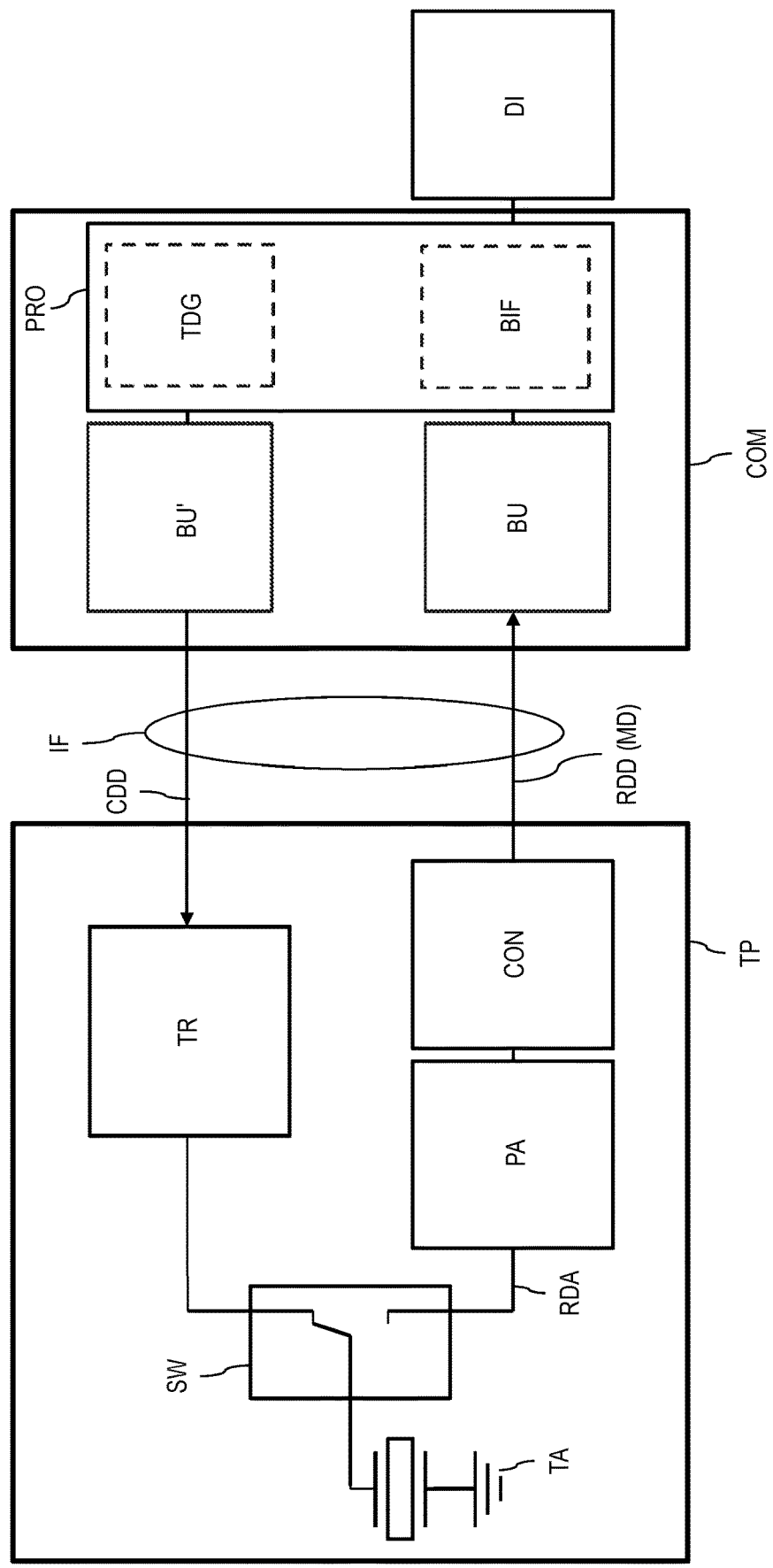
FIG. 2 shows a schematic view of an embodiment of an ultrasonic apparatus according to the invention.

The above disadvantages are eliminated by the embodiment of an ultrasonic apparatus according to the invention, which is shown in FIG. 2. Like the apparatus shown in FIG. 1, this ultrasonic apparatus comprises a movable transducer probe TP with a transducer array TA consisting of electroacoustic transducers. Similar to the transducer probe of FIG. 1, the transducer probe of FIG. 2 is also pressed manually against the patient's body to be examined in order to examine the tissue under the pressing position of the transducer probe by means of ultrasonic waves.

In contrast to the transducer probe of FIG. 1, the transducer probe of FIG. 2 contains, in addition to transducer array TA, further components which are part of scanner box SB in the embodiment of FIG. 1. These are switch array SW, transmitter TR as well as preamplifier PA and analog-to-digital converter CON. These components work analogously as in FIG. 1, so that they are not described in detail again. In particular, the analog raw data output via the switch array, which are designated with RDA in FIG. 2, are first amplified via preamplifier PA and then digitized in analog-to-digital converter CON.

It is now essential to the invention that the digital data generated by the analog-to-digital converter are not immediately subjected to beamforming, but are first buffered in order to subsequently perform the beamforming on the buffered data asynchronously to the clocking of the analog-to-digital converter. To make this possible, the digital raw data output from analog-to-digital converter CON are directly (i.e. without buffering) transferred to a digital data interface IF, which writes the data into buffer memory BU, which is preferably a circular buffer. The raw data transmitted via digital data interface IF are designated with the reference sign RDD in FIG. 2. These raw data contain respective measurement data sets for corresponding measurement time intervals, wherein the structure of the measurement data sets has already been explained above. The measurement data sets are generally designated with the reference sign MD in FIG. 2. Buffer memory BU is part of a separate computer device COM, which is preferably a conventional PC. The computer device is therefore a separate unit which does not belong to the transducer probe.

In the embodiment described here, a bidirectional interface based on the PCI Express standard is used as digital data interface IF. Provided that the data rate of the raw data output from the analog-to-digital converter is reached, any version of this standard can be used, wherein currently the versions 1.0/1.1, 2.0/2.1, 3.0/3.1, 4.0 and 5.0 are known. Likewise, the number of lines used for data transmission can be chosen differently, wherein the use of one, two, four, eight and sixteen lines is currently known. For example, PCIe3× 16 (PCI Express version 3.0/3.1 with 16 lines) or PCIe2×8 (PCI Express version 2.0/2.1 with eight lines) can be used as the data interface. In the embodiment described here, the PCI Express interface is also used for the below described transmission of digital control data CDD from computer COM to high voltage transmitter TR. The data transfer mechanism via interface IF has the capability of directly reading and writing from/into buffer memory BU and also from/into buffer memory BU' described below. In this way, the data transfer rates and the transfer latency do not depend on the response times of the operating system of computer device COM.

Buffer memory BU has a size such that a plurality of consecutive measurement data sets MD are stored in it at the same time. The stored measurement data sets are processed in blocks. During this processing, a beamforming and the generation of reconstructed images for displaying on display DI is carried out by means of a software BIF (BIF=Beam and Image Former) running on processor PRO of computer device COM.

The beamforming is carried out according to the same principle as in beamformer BF of FIG. 1, however, during the beamforming it is possible to access several times on the samples of the respective buffered measurement data sets, since these are buffered for a certain period of time in buffer memory BU. As a result, a reconstructed image of the entire tissue sector with a plurality of different angular directions and tissue depths is obtained for a respective measurement data set during the beamforming. In other words, only a single measurement data set is required to reconstruct an image of the entire tissue sector, whereas in the ultrasonic apparatus of FIG. 1 several measurement data sets are required to obtain a reconstructed image of the tissue sector.

The images reconstructed by means of the beamforming are then converted into an image stream using software BIF. Preferably, several temporally consecutive reconstructed images are averaged and displayed as a single image on display DI. The image sequence shown on display DI preferably has an image refresh rate that is above the flicker frequency of the human eye, e.g. a refresh rate of 60 Hz or 75 Hz. A synchronizable display having an adjustable image refresh rate is used as display DI. This allows to compensated for limited short-term fluctuations in the image rate of the image stream. Such synchronizable displays are known per se. For example, these are displays of the type AMD Freesync or Nvidia G-Sync.

The ultrasonic apparatus of FIG. 2 further differs from the apparatus of FIG. 1 in that control data CDD, which are used to set the transmitting and receiving modes of the electroacoustic transducers for the consecutive measurements, are also generated in computer device COM. For this purpose, software TDG (TDG=Transmit Data Generator) is used, which runs on processor PRO of computer device COM. These control data are buffered in a buffer memory BU', which can be realized as a circular buffer like buffer memory BU. Control data CDD are read out from buffer BU' by high voltage transmitter TR directly via interface IF without further buffering. In accordance with the control data, the high voltage transmitter then generates the high voltages required to transmit an ultrasonic signal by means of the respective transducers in transmitting mode. The control data also specify which transducers are to be operated at which times in transmitting or receiving mode. According to this information the switches of switch array SW are then switched by signals of high voltage transmitter TR. By using buffer BU', the transmission of control data CDD is no longer dependent on response times of the operating system of computer device COM.

A usual configuration of an ultrasonic apparatus comprises 128 electroacoustic transducers, using for example a sample of the ultrasonic echoes of 2 bytes and a sampling rate of 15 MHz for a measurement time interval of 200 µs. This results in a data quantity of 750 kB, and thus, a data rate of approximately 4 GB/s. Consequently, in such a case, the data rate of data interface IF in the direction towards buffer BU should be 4 GB/s or more. When 125 data sets are stored, buffer memory BU must be several 100 MB in size. A typical sampling rate for driving the transducers is 15 MHz with a 2-bit sampling value for each transducer. This also results in a data rate of 4 GB/s, which in this case must be provided at the least by interface IF in the direction towards high voltage transmitter TR.

The embodiment of the invention as described above has a number of advantages. In particular, a central processing unit in the form of a computer COM processes the buffered received data into images block by block asynchronously and decoupled from the ongoing measurements of the transducer. The absence of a measurement synchronous clocking of a beamformer enables the implementation of the beamforming based on software by means of standard hardware components which are usually installed in PCs. In the software, the beamforming can thus be combined with the image forming for generating the images on the display.

The buffering of the digitized raw data in a buffer memory allows multiple accesses and thus a sequential reconstruction of a complete image information of a tissue sector, i.e. for a plurality of angular directions and tissue depths. Thus, a complete two- or possibly three-dimensional image can be obtained from a single measurement data set without multiplying beamforming calculation values.

In addition, the image reconstruction described above is carried out based on data of a moving time interval. This allows achieving a substantially constant image rate which is independent of the timing of the measurements carried out in parallel by means of the transducer probe. An image rate above the flicker frequency of the human eye is advantageous, as already mentioned above. Furthermore, a synchronizable display is preferably used for displaying the image sequence in order to compensate for short-term fluctuations in the image rate.

The invention claimed is:

1. An ultrasonic apparatus for medical examination using ultrasonic waves, comprising:
   a computer device including:
      a raw data buffer memory configured to buffer digital raw data; and
      a control data buffer memory configured to buffer digital control data; and
   a movable transducer probe coupled to the computer device by a digital data inte rface, the movable transducer probe configured to be positioned on a body of a patient and including:

a transducer array of electroacoustic transducers configured to transmit ultrasonic signals into the body and to receive, as analog raw data, ultrasonic echoes of the transmitted ultrasonic signals;

an analog-to-digital converter (CON) directly coupled to the computer device via the digital data interface to directly stream the digital raw data to the computer device, the CON configured to generate the digital raw data in dependence on the received analog raw data, wherein the digital raw data is unbeamformed data to be stored in the raw data buffer memory and comprise measurement data sets for temporally consecutive measurement time intervals, wherein a respective measurement data set comprises ultrasonic echoes from a tissue sector of the body, which result from a transmitting operation of one or more ultrasonic signals by at least one transducer in a transmitting mode, as samples for sampling instants of the respective measurement time interval for a plurality of receiving channels from, respectively, at least one transducer in a receiving mode; and a high voltage transmitter configured to read out digital control data from the control data buffer memory directly via the digital data interface or an additional digital data interface between the movable transducer probe and the computer device and, based on the read out digital control data, to control the transducers of the transducer array;

wherein the buffered streamed digital raw data is the same as the digital raw data, wherein the computer device is configured to carry out a respective digital beamforming for the buffered measurement data sets by time-delayed addition of samples, to determine image values for a plurality of tissue locations at different tissue depths and with several tissue locations for each tissue depth, thereby to obtain a reconstructed image of the tissue sector, to generate, based on the reconstructed images, an image stream of consecutive reconstructed images or of images calculated therefrom with a predetermined image refresh rate, and to supply it to a display which reproduces the image stream, wherein the computer device is configured to determine digital control data based on which the operation of the transducers of the transducer array for transmitting ultrasonic signals and for receiving ultrasonic echoes is determined for the consecutive measurement time intervals, and further wherein the movable transducer probe is configured to read the digital control data via the digital data interface or an additional digital data interface between the movable transducer probe and the computer device and, based on these read-out control data, to control the transducers of the transducer array.

2. The ultrasonic apparatus according to claim 1, wherein the raw data buffer memory is arranged for the simultaneous buffering of a plurality of consecutive measurement data sets.

3. The ultrasonic apparatus according to claim 2, wherein the computer device is configured to determine respective reconstructed images in parallel for several of the plurality of buffered measurement data sets.

4. The ultrasonic apparatus according to claim 1, wherein the computer device is configured such that the images of the image stream are each calculated as an averaging of a plurality of consecutive reconstructed images.

5. The ultrasonic apparatus according to claim 1, wherein the predetermined image refresh rate is 50 Hz or more.

6. The ultrasonic apparatus according to claim 1, wherein the digital data interface comprises a wired data interface and/or a wireless data interface.

7. The ultrasonic apparatus according to claim 1, wherein the digital data interface comprises a PCI Express interface.

8. The ultrasonic apparatus according to claim 1, wherein the high voltage transmitter is configured to generate voltage signals which are supplied via a switch array of transmit-receive switches to the transducer array for generating ultrasonic waves by one or more transducers in transmitting mode, and wherein the transducers of the transducer array can be switched by the switch array into the transmitting mode or the receiving mode.

9. The ultrasonic apparatus according to claim 1, wherein the movable transducer probe further comprises a preamplifier configured to amplify the analog raw data before supplying it to the CON.

10. The ultrasonic apparatus according to claim 1, wherein the movable transducer probe is configured to control the transducers of the transducer array based on reading out the control data buffer memory of the computer device without buffering the digital control data within the movable transducer probe.

* * * * *